United States Patent
Hayward et al.

(10) Patent No.: US 6,553,809 B1
(45) Date of Patent: Apr. 29, 2003

(54) METHOD AND APPARATUS FOR DETECTING HOLES IN PLASTIC CONTAINERS

(75) Inventors: Donald W. Hayward, Waterville, OH (US); David A. Bogstad, Perrysburg, OH (US); Donald Wayne Miller, Waterville, OH (US)

(73) Assignee: Plastic Technologies, Inc., Holland, OH (US)

( * ) Notice: Subject to any disclaimer, the term of this patent is extended or adjusted under 35 U.S.C. 154(b) by 0 days.

(21) Appl. No.: 10/004,362

(22) Filed: Nov. 1, 2001

(51) Int. Cl.[7] ............................................... G01M 3/04
(52) U.S. Cl. ..................................... 73/40.5 A; 73/41
(58) Field of Search ............................. 73/40, 40.5 A, 73/45, 45.1, 45.2, 45.3, 41, 49.2

(56) References Cited

U.S. PATENT DOCUMENTS

| | | | | |
|---|---|---|---|---|
| 3,399,563 A | * | 9/1968 | Helms | 73/45.2 |
| 3,792,606 A | * | 2/1974 | Munger | 73/40 |
| 3,795,137 A | * | 3/1974 | Lo et al. | 73/45.4 |
| 3,841,468 A | * | 10/1974 | Eggert | 198/221 |
| 4,096,736 A | * | 6/1978 | Moshier | 73/40 |
| 4,120,193 A | * | 10/1978 | Tomsic et al. | 73/40 |
| 4,221,124 A | * | 9/1980 | Jones | 73/40 |
| 4,485,668 A | | 12/1984 | Hudson et al. | |
| 4,491,013 A | * | 1/1985 | Bubik | 73/146 |
| 4,677,679 A | * | 6/1987 | Killion | 381/74 |
| 4,809,538 A | * | 3/1989 | Fisch | 73/40.5 A |
| 5,161,408 A | | 11/1992 | McRae et al. | |
| 5,448,907 A | * | 9/1995 | Jensen et al. | |
| 5,602,327 A | | 2/1997 | Torizuka et al. | |
| 5,675,506 A | | 10/1997 | Savic | |
| 5,917,193 A | | 6/1999 | Schroff et al. | |
| 6,330,821 B1 | * | 12/2001 | Arnold et al. | 73/40 |
| 6,401,524 B1 | * | 6/2002 | Incavo et al. | 73/40 |

* cited by examiner

*Primary Examiner*—Helen Kwok
*Assistant Examiner*—Charles Garber
(74) *Attorney, Agent, or Firm*—Donald R. Fraser

(57) ABSTRACT

The invention relates to a method and apparatus for monitoring the production of blow molded plastic containers. It has been discovered that by sonically monitoring the production of a plastic blow molded container, the occurrence of a hole in the wall of the container being formed by a blow molding operation will produce a detectable noise signal. The noise signal is caused by the flow of pressure fluid through the hole. The flow of pressure fluid is caused by the pressure differentiating between the inside and the outside of the container being produced. The noise signal is of an amplitude and frequency readily recognizable from the ambient background noise.

14 Claims, 2 Drawing Sheets

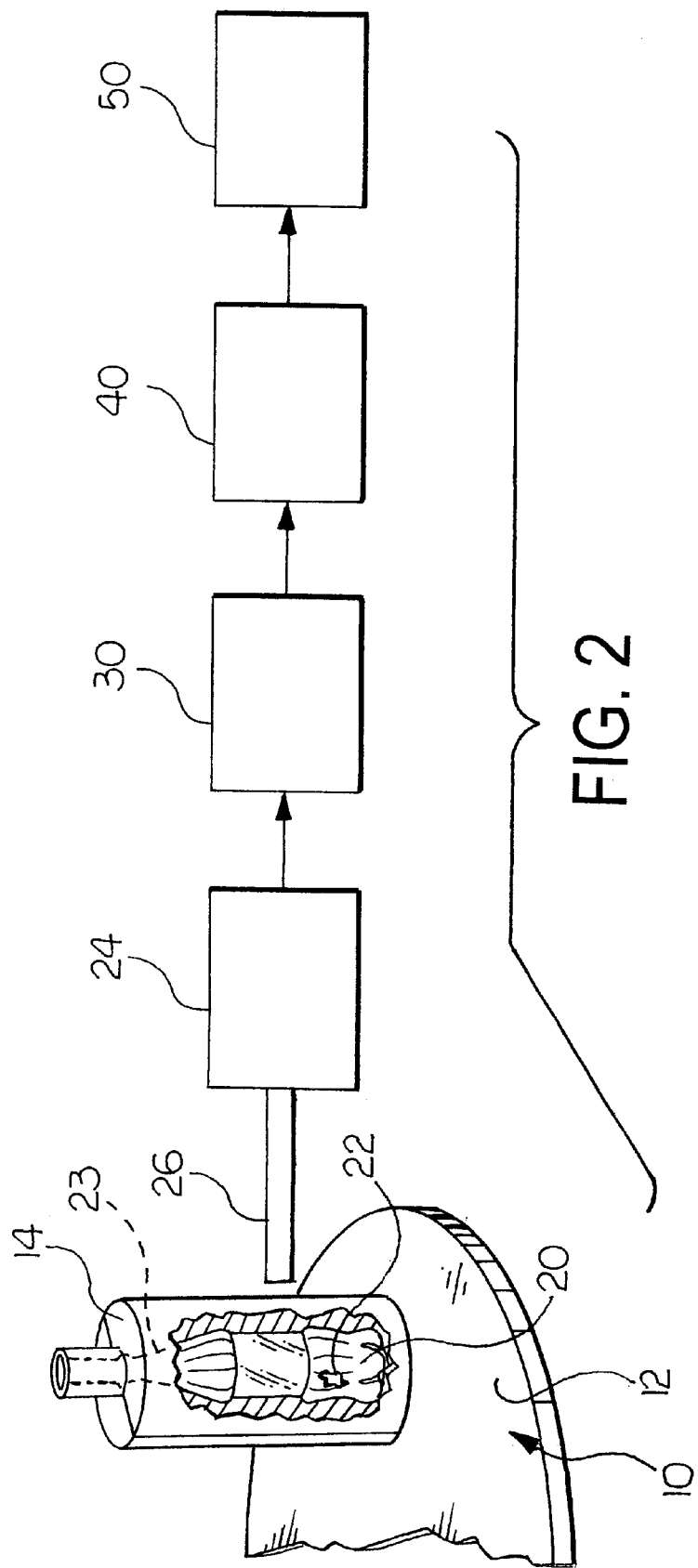

METHOD AND APPARATUS FOR DETECTING HOLES IN PLASTIC CONTAINERS

BACKGROUND OF THE INVENTION

1. Field of the Invention

The invention relates to a method and apparatus for monitoring the production of plastic blow molded containers. More particularly, the invention contemplates the sensing of defects caused by the formation of holes in the walls of plastic blow molded containers by monitoring the sound adjacent predetermined location along the production line of plastic blow molded containers.

2. Description of the Prior Art

The leak testing of tanks, pressure vessels, and containers is an important manufacturing consideration in many different industries. In some instances, the gas-tight or liquid tight integrity of these components is usually determined by some form of a pressure-decay test. With this technique, the unit under test is injected with air to some specified overpressure, and the pressure is monitored for a specified period of time. If the pressure does not decay below a specified value at the end of the designated time period, the component under test is considered to be leak-free.

Another technique involves drawing a vacuum on the component being tested and then completely surrounding it with helium gas. A detector inside the vacuum system notifies the operator if helium is present in the air being pumped from the component.

Still another method involves the pressurization/immersion technique which consists of pressurizing the component, totally immersing the component in water or some other clear liquid, and observing the point of bubble emergence.

Yet another method utilizes a collimated beam of light which is scanned across the component under test. The test component has been pressurized with a tracer gas that strongly absorbs the light. When the light passes through the gas emerging from the source of the leak, the light energy absorbed by the gas produces an acoustic emission which is detected by a microphone. The resulting signal may be processed either as an alarm or it may be processed in coordination with the beam scanning mechanism to indicate exactly where the leak is located.

Another method involves apparatus adopted to detect the sound issued outwardly by the individual blow-molding dies during the blow-molding process wherein the sound is converted to an electrical signal and is compared with a reference signal or level and the faulty burst container is rejected.

SUMMARY OF THE INVENTION

Amongst the objectives of the present invention is to produce a method and apparatus for monitoring the production of blow molded plastic containers to detect the presence of a hole in the container during production of the containers.

Another object of the invention is to produce a method and apparatus that will detect the presence of a hole in a container being formed by a blow molding process.

Another object of the invention is to produce a method and apparatus for detecting a hole in the wall of a plastic container and producing a signal in response thereto.

The above as well as other objects of the invention may typically be achieved by a method and apparatus for monitoring the production of blow molded plastic containers comprising the steps of introducing pressure fluid to the interior of a plastic container being formed by a blow molding process;

acoustically sensing the sound of pressure fluid travelling through a hole in the plastic container being formed;

producing a control signal in response to the sound produced by the pressure fluid travelling through the hole in the plastic container; and sensing the amplitude of the control signal to operatively identify the container with the hole.

BRIEF DESCRIPTION OF THE DRAWINGS

Other objects and advantages of the invention will become readily apparent to those skilled in the art from reading the following detailed description of a preferred embodiment of the invention when considered in the light of the accompanying drawings in which:

FIG. 2 is a block diagram of a system for sensing a hole in a plastic blow molded container during the production thereof.

DETAILED DESCRIPTION OF THE PREFERRED EMBODIMENT

Figure 1:
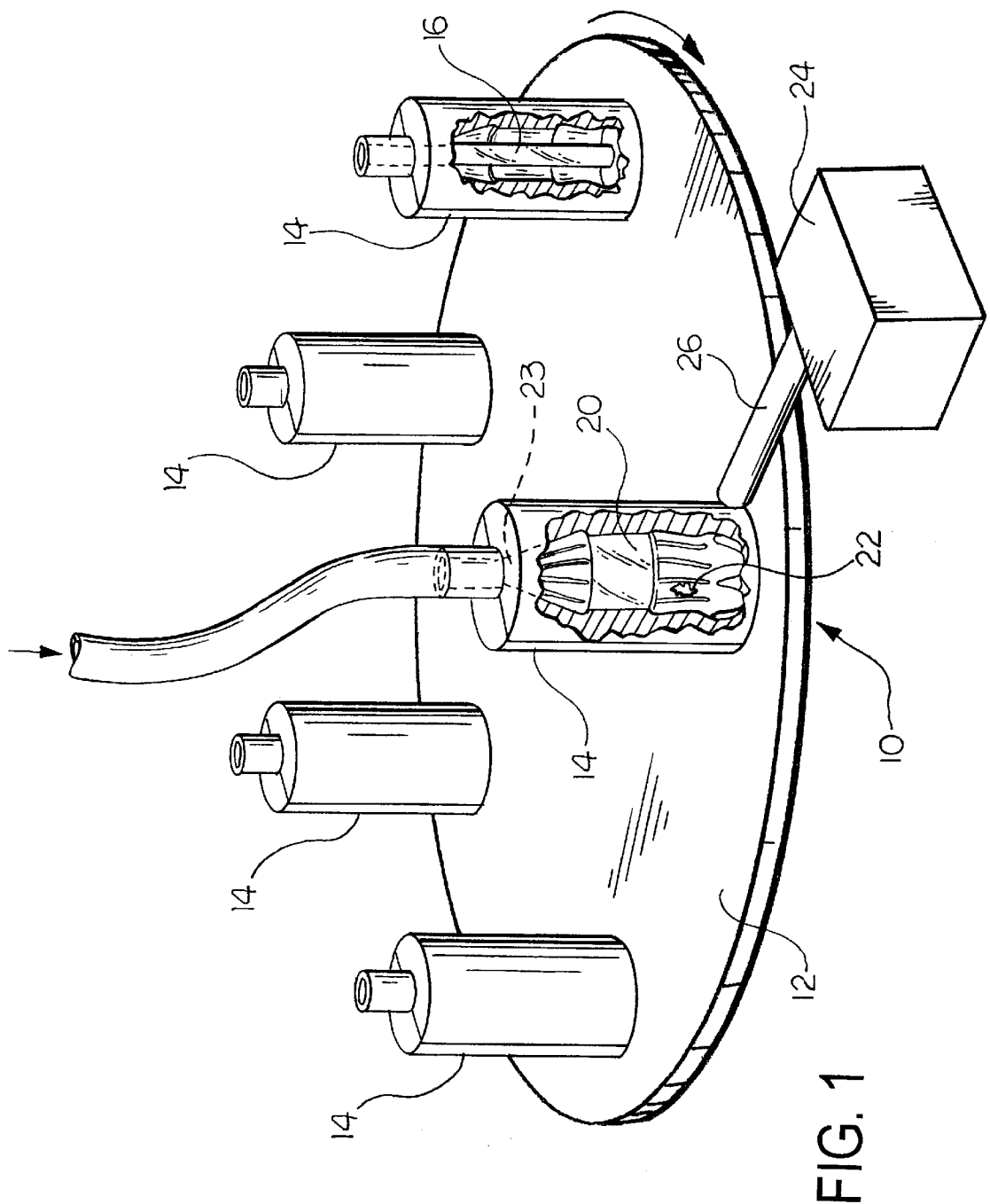
FIG. 1 is an enlarged view of the sensing tube placed in proximity to the plastic containers being formed to convey an acoustical signal created by the flow of pressure fluid through a hole in the container being formed during a blow molding operation.

Referring to the drawings, there is illustrated a system incorporating the features of the invention, and more particularly disclosing a station along the production line of a typical blow molding machine.

The typical blow molding machines include an annular rotatably mounted platform capable of serially receiving hollow plastic preforms or parisons. The preforms are carried in molds having an inner cavity in the desired configuration or shape of the finished container to be formed. The preforms are heated to a predetermined temperature, which prepares the plastic material to be readily blow molded. Upon reaching the desired temperature, high pressure fluid, such as compressed air, is sequentially introduced into the hollow interior of the preforms. The preforms are thereby caused to expand and assume the shape of the associated mold. The containers are caused to be inspected for defects. In the event a defective container is detected, means are provided for rejecting the container prior to filling or storage.

The completed plastic containers are then transferred, from the annular rotating platform to a conveyor which transports the containers to a filling station. Finally, the filled containers are suitably removed from the conveyor to be stored for later delivery or are immediately loaded on appropriate vehicles for delivery to the ultimate customer. Obviously, unfilled containers may also be off-loaded in a similar fashion.

There are certain instances in which, due to a myriad of reasons, the completed containers have undetected faults such as, for example, minute holes or apertures in the walls of the containers. When these faulty containers are subsequently filled with a fluid such as a carbonated beverage, disastrous results occur. Accordingly, it has become extremely important to develop a method and apparatus for the detection of these difficult to detect faults in plastic containers.

The drawings disclose an apparatus generally indicated by reference numeral 10 positioned in proximity of the annular rotating platform 12 of a blow-molding machine of the type manufactured by Side1, a corporation of France. The rotating platform 12 contains an annular array of mold cavities 14 into which heated plastic preforms 16 are indexed to a source 18 of pressure fluid which in most instances is compressed air. The pressure fluid is introduced into the hollow interior of the heated preform 16 causing the preform to expand and assume the shape of the interior of the mold cavity 14 as a completed container 20. In the event a hole 22 is caused to be formed in the wall of the container 20, the pressure fluid from the source 18 escaping through the hole 22 will create an acoustic signal.

A sound detector 24 is positioned adjacent the periphery of the rotating platform 12. The input of the sound detector 24 is coupled to a sound columnator 26. The sound columnator 26 is formed of a hollow plastic tube having the distal end thereof pointed in the direction of the container 20. The sound detector 24 suitable for the purposes of the invention is commercially available and identified as Radio Shack Sound Level Meter Model 33-2050 having an output of from 0 to 1 volt D.C.

As illustrated in FIG. 2, the output of the sound detector 24 is coupled to the input of an amplifier and discriminator 30 which may be set to produce an output signal based upon the amplitude of the voltage signal produced by the sound level meter 26 which may be fed to a logic circuit 40 consisting of timing and/or counting and control logic.

The logic circuit 40 may be coupled to an air blow-off station 50 which is disposed downstream of the acoustic sensor and is effective to remove any defective container sensed by the logic circuit 40. Typically, the air blow-off station 50 includes solenoid operated valves controlling the flow of pressure fluid, such as compressed air for example, to forcefully eject a defective container.

It has been surprisingly discovered that the sound columnator 26 tends to both focus the transmission of sound energy caused by the pressure fluid flowing through the hole 22 in the container 20, but also tends to intensify the sound energy as it passes from the hole 22 to the sound detector 24.

Further, it has been found that satisfactory results are achieved by utilizing a plastic tube twelve inches in length and forming of a rigid polyvinyl chloride (PVC) having a nominal I.D. of 1.0 inch, and an O.D. of 1.3 inches.

In operation, the apparatus illustrated in FIG. 1 is placed adjacent the blow molding machine so that the open end of columnator 26 of the sound detector 24 faces the cavity 14 wherein the pressure fluid is injected into the heated preform 16 to cause the preform to expand to form a completed container 20.

Should the container 20 contain a fault such as a hole 22, or a defect in the finish 23 of the container 20, the escaping pressure fluid flowing there through would create an acoustic signal which would be sensed by the columnator 26 and thence the sound detector 24. The sound detector 24 would produce an electric signal in response to the acoustic signal and the electric signal would be sent to the amplifier and discriminator circuit 30.

The signal received from the sound detector 24 is amplified and the amplified signal is sent to the logic circuit 40. The logic circuit 40 is operative to coordinate and keep tract of the subsequent path of the container facing a hole in the wall thereof and will send an appropriately timed signal to the air blow-off station 50. The station 50 contains solenoid-operated valves controlling the flow of pressurized air capable of completing the rejection operation. The pressurized air will then be appropriate to remove the container housing the hole from the production line.

In accordance with the provisions of the patent statutes, the present invention has been described in what is considered to represent its preferred embodiment. However, it should be understood that the invention can be practiced otherwise than as specifically illustrated and described without departing from it's spirit or scope.

What is claimed is:

1. A method for monitoring the production of blow molded plastic containers for detecting a hole in the container comprising the steps of:

introducing pressure fluid to the interior of a preform in a mold cavity to form a blow molded plastic container;

acoustically sensing the sound of pressure fluid travelling through a hole in a wall of the container;

providing a rigid columnator adjacent the mold cavity to focus and intensify the sound produced by the pressure fluid travelling through the hole in the plastic container; and producing a control signal in response to the focused and intensified sound from the columnator.

2. The method defined in claim 1 wherein the step of producing a control signal includes amplifying the control signal.

3. The method defined in claim 2 further including the step of rejecting the container having a hole therein.

4. The method defined in claim 3 wherein said step of rejecting the container includes directing pressure fluid to reject the container having a hole therein.

5. The method defined in claim 1 wherein the step of providing a columnator includes forming the columnator as a tube of polyvinyl chloride material.

6. The method defined in claim 5 further including forming the tube with a length of approximately twelve inches, an inner diameter of approximately one inch and an outer diameter of approximately 1.3 inches.

7. Apparatus for monitoring the production of blow molded plastic containers for detecting a hole in the container comprising:

a conduit for introducing pressure fluid to the interior of preforms in mold cavities to form blow molded plastic containers during the production of the containers;

a sensor for sensing the sound of pressure fluid travelling through a hole in one of the containers and for producing a control signal in response to the sound;

a columnator included in said sensor for focusing and intensifying the sound, said columnator being formed as a rigid tube having an open end adjacent the mold cavity containing the one container; and a container rejecter for receiving the control signal produced by said sensor for rejecting the one container having the hole therein.

8. Apparatus as defined in claim 7 wherein said cylinder is formed of a plastic material.

9. Apparatus as defined in claim 8 wherein said plastic material is polyvinyl chloride.

10. Apparatus as defined in claim 7 wherein said columnator has a length of approximately twelve inches.

11. Apparatus as defined in claim 7 wherein said columnator has an inner diameter of approximately one inch.

12. Apparatus as defined in claim 11 wherein said columnator has an outer having diameter of approximately 1.3 inches.

13. Apparatus as defined in claim 7 wherein said sensor includes a sound detector having an input coupled to an end of said columnator opposite said open end.

14. A method for monitoring the production of blow molded plastic containers for detecting a hole in the container comprising the steps of:

introducing pressure fluid to the interior of heated preforms in mold cavities to form blow molded plastic containers during the production of the containers;

providing a rigid columnator and positioning a distal end of the columnator adjacent a path of travel of the mold cavities during said introducing of fluid pressure;

acoustically sensing the sound of pressure fluid travelling through an incomplete finish of a one of the containers with the columnator; and producing a control signal in response to the focused and intensified sound from the columnator for rejecting the one container.

\* \* \* \* \*

(12) EX PARTE REEXAMINATION CERTIFICATE (5810th)
United States Patent
Hayward et al.

(10) Number: US 6,553,809 C1
(45) Certificate Issued: Jul. 10, 2007

(54) METHOD AND APPARATUS FOR DETECTING HOLES IN PLASTIC CONTAINERS

(75) Inventors: Donald W. Hayward, Waterville, OH (US); David A. Bogstad, Perrysburg, OH (US); Donald Wayne Miller, Waterville, OH (US)

(73) Assignee: Plastic Technologies, Inc., Holland, OH (US)

Reexamination Request:
No. 90/007,109, Jul. 7, 2004

Reexamination Certificate for:
Patent No.: 6,553,809
Issued: Apr. 29, 2003
Appl. No.: 10/004,362
Filed: Nov. 1, 2001

(51) Int. Cl.
*G01M 3/04* (2006.01)

(52) U.S. Cl. .................... 73/40.5 A; 73/41
(58) Field of Classification Search ............... 73/40, 73/40.5 R, 40.5 A, 41, 41.2–41.4, 45, 45.1, 73/45.2, 45.3, 45.4, 49.2, 49.3, 49.4
See application file for complete search history.

(56) References Cited

U.S. PATENT DOCUMENTS

| | | | | |
|---|---|---|---|---|
| 1,647,253 A | * | 11/1927 | Satterlee | 181/193 |
| 1,814,357 A | * | 7/1931 | Wolff et al. | 181/158 |
| 2,324,305 A | * | 7/1943 | Kurtz | 356/25 |
| 3,290,922 A | * | 12/1966 | Thompson | 73/52 |
| 3,711,845 A | * | 1/1973 | Chasek | 342/351 |
| 3,802,252 A | * | 4/1974 | Hayward et al. | 73/52 |
| 3,831,561 A | * | 8/1974 | Yamamoto et al. | 122/379 |
| 4,287,581 A | * | 9/1981 | Neale, Sr. | 340/605 |
| 4,635,042 A | * | 1/1987 | Andrews | 340/605 |
| 4,785,908 A | * | 11/1988 | Rothenberg | 181/156 |
| 5,101,774 A | * | 4/1992 | Marziale et al. | 122/504.2 |
| 5,824,884 A | * | 10/1998 | Olender et al. | 73/40.5 A |
| 5,955,670 A | * | 9/1999 | Goodman et al. | 73/592 |
| 6,220,098 B1 | * | 4/2001 | Johnson et al. | 73/592 |
| 6,416,308 B1 | | 7/2002 | Pena | |

FOREIGN PATENT DOCUMENTS

WO WO01/64425 9/2001

OTHER PUBLICATIONS

"Sound Waves and Music, Lesson 5: Musical Instruments" from website entitled The Physics Classroom located at URL (http://www.physicsclassroom.com/Class/sound/U11L5a.html).*

Langridge, Graham, "Physics Lab Demonstration", available on the Internet at <http://www.physics.ubc.ca>.*

PVC (Polyvinylchloride) to San Diego Plastics, Inc., available on the Internet at <http://www.sdplastics.com/pvc.html>.*

* cited by examiner

Primary Examiner—Erik Kielin

(57) ABSTRACT

The invention relates to a method and apparatus for monitoring the production of blow molded plastic containers. It has been discovered that by sonically monitoring the production of a plastic blow molded container, the occurrence of a hole in the wall of the container being formed by a blow molding operation will produce a detectable noise signal. The noise signal is caused by the flow of pressure fluid through the hole. The flow of pressure fluid is caused by the pressure differentiating between the inside and the outside of the container being produced. The noise signal is of an amplitude and frequency readily recognizable from the ambient background noise.

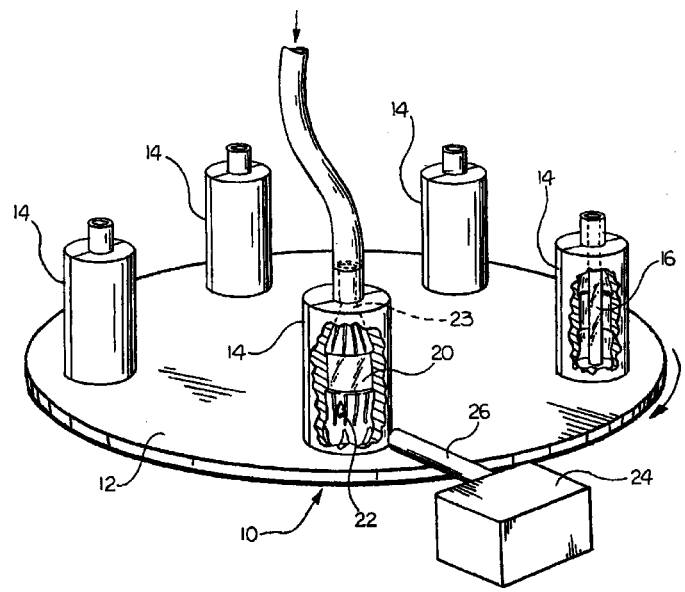

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 7, 8 and 14 are determined to be patentable as amended.

Claims 2-6 and 9-13, dependent on an amended claim, are determined to be patentable.

1. A method for monitoring the production of blow molded plastic containers for detecting a hole in the container comprising the steps of:
    introducing pressure fluid to the interior of a preform in a mold cavity to form a blow molded plastic container;
    acoustically sensing the sound of pressure fluid travelling through a hole in a wall of the container;
    providing a [rigid] columnator adjacent the mold cavity *during at least a portion of the step of introducing* to focus and intensify the sound produced by the pressure fluid travelling through the hole in the plastic container, *the columnator being a straight rigid tube of substantially uniform cross section*; and
    producing a control signal in response to the focused and intensified sound from the columnator.

7. Apparatus for monitoring the production of blow molded plastic containers for detecting a hole in the container comprising:
    a conduit for introducing pressure fluid to the interior of preforms in mold cavities to form blow molded plastic containers during the production of the containers;
    a sensor for sensing the sound of pressure fluid travelling through a hole in one of the containers and for producing a control signal in response to the sound;
    a columnator included in said sensor for focusing and intensifying the sound, said columnator being formed as a *straight* rigid tube *of uniform cross section* having an open end adjacent the mold cavity containing the one container *when the fluid pressure is being introduced to the mold cavity*; and
    a container rejecter for receiving the control signal produced by said sensor for rejecting the one container having the hole therein.

8. Apparatus as defined in claim 7 wherein said [cylinder] *columnator* is formed of a plastic material.

14. A method for monitoring the production of blow molded plastic containers for detecting a hole in the container comprising the steps of:
    introducing pressure fluid to the interior of heated preforms in mold cavities to form blow molded plastic containers during the production of the containers;
    providing a rigid columnator *formed as a straight tube of substantially uniform cross section* and positioning a distal end of the columnator adjacent a path of travel of the mold cavities *wherein the distal end is adjacent each of the mold cavities* during said introducing of fluid pressure;
    acoustically sensing the sound of pressure fluid travelling through an incomplete finish of a one of the containers with the columnator; and
    producing a control signal in response to the focused and intensified sound from the columnator for rejecting the one container.

* * * * *